United States Patent
Gomez et al.

(10) Patent No.: US 9,084,623 B2
(45) Date of Patent: Jul. 21, 2015

(54) CONTROLLER ASSISTED RECONFIGURATION OF AN ARTICULATED INSTRUMENT DURING MOVEMENT INTO AND OUT OF AN ENTRY GUIDE

(75) Inventors: Daniel Gomez, Mountain View, CA (US); Nicola Diolaiti, Palo Alto, CA (US); David Q. Larkin, Menlo Park, CA (US); Paul E. Lilagan, Sunnyvale, CA (US); Probal Mitra, Mountain View, CA (US); Tabish Mustafa, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 609 days.

(21) Appl. No.: 12/613,328

(22) Filed: Nov. 5, 2009

(65) Prior Publication Data

US 2011/0040305 A1   Feb. 17, 2011

Related U.S. Application Data

(63) Continuation-in-part of application No. 12/541,913, filed on Aug. 15, 2009, now Pat. No. 8,903,546.

(51) Int. Cl.
    *A61B 19/00* (2006.01)

(52) U.S. Cl.
    CPC ............. *A61B 19/2203* (2013.01); *A61B 19/56* (2013.01); *A61B 2019/223* (2013.01); *A61B 2019/2292* (2013.01)

(58) Field of Classification Search
    CPC ............ A61B 19/2203; A61B 19/56; A61B 2019/2207; A61B 2019/2223; A61B 2019/223; A61B 2019/2269; A61B 2019/2273; A61B 2019/2276; A61B 2019/228; A61B 2019/2284; A61B 2019/562; A61B 2019/568; B25J 9/10; B25J 9/1005; B25J 9/101; B25J 9/1015; B25J 9/16; B25J 9/1605; B25J 9/161; B25J 9/1656; B25J 9/1658; B25J 9/1661; B25J 9/1664
    USPC .................................................. 606/130, 205
    See application file for complete search history.

(56) References Cited

U.S. PATENT DOCUMENTS

| 4,577,621 A | 3/1986 | Patel |
| 4,644,237 A | 2/1987 | Frushour et al. |

(Continued)

FOREIGN PATENT DOCUMENTS

| EP | 812662 A1 | 12/1997 |
| EP | 1125557 A2 | 8/2001 |

(Continued)

OTHER PUBLICATIONS

Vertut, Jean and Phillipe Coiffet, *Robot Technology: Teleoperation and Robotics Evolution and Development*, English translation Prentice-Hall, Inc., Inglewood Cliffs, NJ, USA 1986, vol. 3A, 332 pages.

(Continued)

*Primary Examiner* — Katherine Dowe
*Assistant Examiner* — Kendra Obu

(57) ABSTRACT

To perform a tool exchange in a medical robotic system, tool is retracted back into an entry guide from a deployed position and pose so that an assistant in the operating room may replace it with a different tool. While the tool is being retracted back towards the entry guide by user action, its configuration is changed to an entry pose while avoiding collisions with other objects so that it may fit in the entry guide. After the tool exchange is completed, a new tool is inserted in the entry guide and extended out of the guide by user action to the original position of the old tool prior to its retraction into the entry guide while the tool's controller assists the user by reconfiguring the new tool so as to resemble the original deployed pose of the old tool prior to its retraction into the entry guide.

20 Claims, 9 Drawing Sheets

(56) References Cited

U.S. PATENT DOCUMENTS

| | | | |
|---|---|---|---|
| 4,791,934 A | 12/1988 | Brunnett | |
| 4,815,450 A | 3/1989 | Patel | |
| 4,831,549 A | 5/1989 | Red et al. | |
| 4,837,703 A | 6/1989 | Kakazu et al. | |
| 4,979,949 A | 12/1990 | Matsen, III | |
| 5,086,401 A | 2/1992 | Glassman et al. | |
| 5,174,276 A | 12/1992 | Crockard | |
| 5,230,338 A | 7/1993 | Allen et al. | |
| 5,251,611 A | 10/1993 | Zehel et al. | |
| 5,337,733 A | 8/1994 | Bauerfeind et al. | |
| 5,343,385 A | 8/1994 | Joskowicz et al. | |
| 5,408,409 A | 4/1995 | Glassman et al. | |
| 5,417,210 A | 5/1995 | Funda et al. | |
| 5,528,955 A | 6/1996 | Hannaford et al. | |
| 5,704,897 A | 1/1998 | Truppe | |
| 5,748,767 A | 5/1998 | Raab | |
| 5,749,362 A | 5/1998 | Funda et al. | |
| 5,755,725 A | 5/1998 | Druais | |
| 5,759,151 A | 6/1998 | Sturges | |
| 5,820,545 A | 10/1998 | Arbter et al. | |
| 5,820,623 A | 10/1998 | Ng | |
| 5,831,408 A | 11/1998 | Jacobus et al. | |
| 5,835,693 A | 11/1998 | Lynch et al. | |
| 5,876,325 A | 3/1999 | Mizuno et al. | |
| 5,950,629 A | 9/1999 | Taylor et al. | |
| 5,987,591 A | 11/1999 | Jyumonji | |
| 6,083,170 A | 7/2000 | Ben-Haim | |
| 6,115,053 A | 9/2000 | Perlin | |
| 6,120,433 A | 9/2000 | Mizuno et al. | |
| 6,184,868 B1 | 2/2001 | Shahoian et al. | |
| 6,204,620 B1 | 3/2001 | McGee et al. | |
| 6,224,542 B1 | 5/2001 | Chang et al. | |
| 6,243,624 B1 | 6/2001 | Wu et al. | |
| 6,325,808 B1 | 12/2001 | Bernard et al. | |
| 6,342,889 B1 | 1/2002 | Callahan | |
| 6,371,909 B1 | 4/2002 | Hoeg et al. | |
| 6,398,726 B1 | 6/2002 | Ramans et al. | |
| 6,424,885 B1 | 7/2002 | Niemeyer et al. | |
| 6,442,417 B1 | 8/2002 | Shahidi et al. | |
| 6,456,901 B1 | 9/2002 | Xi et al. | |
| 6,459,926 B1 | 10/2002 | Nowlin et al. | |
| 6,468,265 B1 | 10/2002 | Evans et al. | |
| 6,493,608 B1 * | 12/2002 | Niemeyer | 700/302 |
| 6,522,906 B1 | 2/2003 | Salisbury, Jr. et al. | |
| 6,550,757 B2 | 4/2003 | Sesek | |
| 6,574,355 B2 * | 6/2003 | Green | 382/128 |
| 6,643,563 B2 | 11/2003 | Hosek et al. | |
| 6,645,196 B1 | 11/2003 | Nixon et al. | |
| 6,648,816 B2 | 11/2003 | Irion et al. | |
| 6,659,939 B2 | 12/2003 | Moll et al. | |
| 6,770,081 B1 | 8/2004 | Cooper et al. | |
| 6,837,883 B2 | 1/2005 | Moll et al. | |
| 6,847,922 B1 | 1/2005 | Wampler, II | |
| 6,926,709 B2 | 8/2005 | Bieger et al. | |
| 6,960,162 B2 | 11/2005 | Saadat et al. | |
| 6,984,203 B2 | 1/2006 | Tartaglia et al. | |
| 6,991,627 B2 | 1/2006 | Madhani et al. | |
| 7,041,053 B2 | 5/2006 | Miyake | |
| 7,155,315 B2 | 12/2006 | Niemeyer et al. | |
| 7,181,315 B2 | 2/2007 | Watanabe et al. | |
| 7,194,118 B1 | 3/2007 | Harris et al. | |
| 7,491,198 B2 | 2/2009 | Kockro | |
| 7,725,214 B2 | 5/2010 | Diolaiti | |
| 7,806,891 B2 | 10/2010 | Nowlin et al. | |
| 7,819,859 B2 | 10/2010 | Prisco et al. | |
| 7,963,913 B2 | 6/2011 | Devengenzo et al. | |
| 7,979,157 B2 | 7/2011 | Anvari | |
| 7,996,110 B2 | 8/2011 | Lipow et al. | |
| 7,998,058 B2 | 8/2011 | Kura et al. | |
| 8,062,288 B2 | 11/2011 | Cooper et al. | |
| 8,108,072 B2 | 1/2012 | Zhao et al. | |
| 8,120,301 B2 | 2/2012 | Goldberg et al. | |
| 8,130,907 B2 | 3/2012 | Maurer, Jr. et al. | |
| 8,155,479 B2 | 4/2012 | Hoffman et al. | |
| 8,170,716 B2 | 5/2012 | Coste-Maniere et al. | |
| 8,256,319 B2 | 9/2012 | Cooper et al. | |
| 8,315,720 B2 | 11/2012 | Mohr et al. | |
| 8,335,590 B2 | 12/2012 | Costa et al. | |
| 8,620,473 B2 * | 12/2013 | Diolaiti et al. | 700/245 |
| 8,864,652 B2 | 10/2014 | Diolaiti et al. | |
| 8,903,546 B2 | 12/2014 | Diolaiti et al. | |
| 2001/0035871 A1 | 11/2001 | Bieger et al. | |
| 2002/0045905 A1 | 4/2002 | Gerbi et al. | |
| 2002/0120188 A1 | 8/2002 | Brock et al. | |
| 2003/0032878 A1 | 2/2003 | Shahidi | |
| 2003/0055410 A1 | 3/2003 | Evans et al. | |
| 2003/0109780 A1 | 6/2003 | Coste-Maniere et al. | |
| 2003/0114730 A1 | 6/2003 | Hale et al. | |
| 2003/0167103 A1 | 9/2003 | Tang et al. | |
| 2003/0220541 A1 | 11/2003 | Salisbury, Jr. et al. | |
| 2003/0225479 A1 | 12/2003 | Waled | |
| 2004/0077940 A1 | 4/2004 | Kienzle et al. | |
| 2004/0106916 A1 | 6/2004 | Quaid et al. | |
| 2004/0225183 A1 | 11/2004 | Michlitsch et al. | |
| 2004/0238732 A1 | 12/2004 | State et al. | |
| 2004/0249508 A1 | 12/2004 | Suita et al. | |
| 2004/0254679 A1 | 12/2004 | Nagasaka | |
| 2005/0022158 A1 | 1/2005 | Launay et al. | |
| 2005/0054895 A1 | 3/2005 | Hoeg et al. | |
| 2005/0059960 A1 | 3/2005 | Simaan et al. | |
| 2005/0096502 A1 | 5/2005 | Khalili | |
| 2005/0113640 A1 | 5/2005 | Saadat et al. | |
| 2005/0203380 A1 | 9/2005 | Sauer et al. | |
| 2005/0228365 A1 | 10/2005 | Wang et al. | |
| 2005/0251113 A1 | 11/2005 | Kienzle, III | |
| 2006/0142657 A1 * | 6/2006 | Quaid et al. | 600/424 |
| 2006/0258938 A1 | 11/2006 | Hoffman et al. | |
| 2006/0261770 A1 | 11/2006 | Kishi et al. | |
| 2007/0013336 A1 | 1/2007 | Nowlin et al. | |
| 2007/0016174 A1 | 1/2007 | Millman et al. | |
| 2007/0032906 A1 | 2/2007 | Sutherland et al. | |
| 2007/0038080 A1 | 2/2007 | Salisbury, Jr. et al. | |
| 2007/0060879 A1 | 3/2007 | Weitzner et al. | |
| 2007/0135803 A1 | 6/2007 | Belson | |
| 2007/0142968 A1 | 6/2007 | Prisco et al. | |
| 2007/0255454 A1 | 11/2007 | Dariush | |
| 2007/0265491 A1 | 11/2007 | Krag et al. | |
| 2007/0270650 A1 | 11/2007 | Eno et al. | |
| 2007/0283970 A1 * | 12/2007 | Mohr et al. | 128/898 |
| 2007/0287884 A1 | 12/2007 | Schena | |
| 2007/0287992 A1 * | 12/2007 | Diolaiti et al. | 606/1 |
| 2008/0004603 A1 | 1/2008 | Larkin et al. | |
| 2008/0033240 A1 * | 2/2008 | Hoffman et al. | 600/109 |
| 2008/0065099 A1 | 3/2008 | Cooper et al. | |
| 2008/0065105 A1 | 3/2008 | Larkin et al. | |
| 2008/0065109 A1 | 3/2008 | Larkin | |
| 2008/0071291 A1 | 3/2008 | Duval et al. | |
| 2008/0081992 A1 | 4/2008 | Kagermeier | |
| 2008/0118115 A1 | 5/2008 | Williamson | |
| 2008/0140087 A1 | 6/2008 | Barbagli | |
| 2008/0161830 A1 | 7/2008 | Sutherland et al. | |
| 2008/0188986 A1 | 8/2008 | Hoppe | |
| 2008/0243142 A1 | 10/2008 | Gildenberg | |
| 2008/0247506 A1 | 10/2008 | Maschke | |
| 2008/0287963 A1 | 11/2008 | Rogers et al. | |
| 2009/0012531 A1 | 1/2009 | Quaid et al. | |
| 2009/0024142 A1 | 1/2009 | Ruiz Morales | |
| 2009/0036902 A1 | 2/2009 | DiMaio et al. | |
| 2009/0088634 A1 | 4/2009 | Zhao et al. | |
| 2009/0192523 A1 | 7/2009 | Larkin et al. | |
| 2009/0192524 A1 | 7/2009 | Itkowitz et al. | |
| 2009/0228145 A1 | 9/2009 | Hodgson et al. | |
| 2009/0248036 A1 | 10/2009 | Hoffman et al. | |
| 2009/0259105 A1 | 10/2009 | Miyano et al. | |
| 2009/0326318 A1 | 12/2009 | Tognaccini et al. | |
| 2009/0326552 A1 | 12/2009 | Diolaiti | |
| 2009/0326553 A1 | 12/2009 | Mustufa et al. | |
| 2009/0326556 A1 | 12/2009 | Diolaiti et al. | |
| 2009/0326711 A1 | 12/2009 | Chang et al. | |
| 2010/0004505 A1 | 1/2010 | Umemoto et al. | |
| 2010/0036198 A1 | 2/2010 | Tacchino et al. | |
| 2010/0106356 A1 | 4/2010 | Trepagnier et al. | |
| 2010/0198232 A1 | 8/2010 | Diolaiti | |
| 2010/0249657 A1 | 9/2010 | Nycz et al. | |

(56) References Cited

U.S. PATENT DOCUMENTS

| | | |
|---|---|---|
| 2010/0274087 A1 | 10/2010 | Diolaiti et al. |
| 2010/0317965 A1 | 12/2010 | Itkowitz et al. |
| 2011/0040404 A1 | 2/2011 | Diolaiti et al. |
| 2011/0071675 A1 | 3/2011 | Wells et al. |
| 2011/0196199 A1 | 8/2011 | Donhowe et al. |
| 2011/0202068 A1 | 8/2011 | Diolaiti et al. |
| 2011/0290856 A1 | 12/2011 | Shelton, IV et al. |
| 2012/0059391 A1 | 3/2012 | Diolaiti et al. |
| 2012/0059392 A1 | 3/2012 | Diolaiti |
| 2012/0132450 A1 | 5/2012 | Timm et al. |
| 2013/0231680 A1 | 9/2013 | Diolaiti et al. |
| 2014/0055489 A1 | 2/2014 | Itkowitz et al. |
| 2014/0135792 A1 | 5/2014 | Larkin et al. |
| 2014/0222021 A1 | 8/2014 | Diolaiti et al. |
| 2014/0232824 A1 | 8/2014 | Dimaio et al. |

FOREIGN PATENT DOCUMENTS

| | | |
|---|---|---|
| JP | S61230895 A | 10/1986 |
| JP | H01280449 A | 11/1989 |
| JP | H0889506 A | 4/1996 |
| JP | H08154321 A | 6/1996 |
| JP | H08275958 A | 10/1996 |
| JP | H11000309 A | 6/1999 |
| JP | 2000300579 A | 10/2000 |
| JP | 2001104333 A | 4/2001 |
| JP | 2001287183 A | 10/2001 |
| JP | 2004223128 A | 8/2004 |
| JP | 2007029232 A | 2/2007 |
| JP | 2009006410 A | 1/2009 |
| JP | 2009012106 A | 1/2009 |
| JP | 2009525097 A | 7/2009 |
| WO | WO-2004014244 | 2/2004 |
| WO | WO-2006079108 A1 | 7/2006 |
| WO | WO-2007030173 A1 | 3/2007 |
| WO | WO-2007047782 A2 | 4/2007 |
| WO | WO-2007088206 A2 | 8/2007 |
| WO | WO-2007088208 A1 | 8/2007 |
| WO | WO-2007136768 A2 | 11/2007 |
| WO | WO-2007146987 A2 | 12/2007 |
| WO | WO-2008002830 A2 | 1/2008 |
| WO | WO-2008103383 A1 | 8/2008 |
| WO | WO-2009034477 | 3/2009 |
| WO | WO-2009037576 | 3/2009 |
| WO | WO-2009158164 A1 | 12/2009 |
| WO | WO-2010039394 A1 | 4/2010 |

OTHER PUBLICATIONS

Bettini , A. et al., "Vision Assisted Control for Manipulation Using Virtual Fixtures," IEEE/RSJ International Conference on Intelligent Robots and Systems (IROS), Oct. 29-Nov. 3, 2001, pp. 171-1176, vol. 2.

Christoforou, E.G. et al., "Robotic Arm for Magnetic Resonance Imaging Guided Interventions," 1st IEEE/RAS-EMBS International Conference on Biomedical Robotics and Biomechatronics, Feb. 20-22, 2006, pp. 911-916.

International Search Report and Written Opinion for Application No. PCT/US2012/064379, mailed on Mar. 29, 2013, 12 pages.

International Search Report and Written Opinion for Application No. PCT/US2012/064400, mailed on Mar. 27, 2013, 10 pages.

Kapoor, Ankur, Motion Constrained Control of Robots for Dexterous Surgical Tasks, Ph.D. Dissertation, The Johns Hopkins University, Department of Computer Science, Baltimore, Maryland, Sep. 2007, 351 pages.

PCT/US07/71850 International Search Report and Written Opinion of the International Searching Authority, mailed Feb. 13, 2009, 9 pages.

PCT/US09/46234 International Search Report and Written Opinion of the International Searching Authority, mailed Sep. 9, 2009, 13 pages.

PCT/US09/56078 International Search Report and Written Opinion of the International Searching Authority, mailed Jan. 20, 2010, 12 pages.

PCT/US10/28886 International Search Report and Written Opinion of the International Searching Authority, mailed Jul. 6, 2010, 11 pages.

PCT/US10/28897 International Search Report and Written Opinion of the International Searching Authority, mailed Jul. 19, 2010, 16 pages.

PCT/US10/38246 International Search Report and Written Opinion of the International Searching Authority, mailed Sep. 14, 2010, 17 pages.

PCT/US2011/036109 International Search Report and Written Opinion of the International Searching Authority, mailed Oct. 19, 2011, 16 pages.

PCT/US2011/036109 Invitation to Pay Additional Fees and Partial International Search Report, mailed Aug. 18, 2011, 5 pages.

Wei, Guo-Quing et al., "Real-Time Visual Servoing for Laparoscopic Surgery," IEEE Engineering in Medicine and Biology Magazine, Jan./Feb. 1997, pp. 40-45, vol. 16—Issue 1, IEEE.

Zhang, Xiaoli and Shahram Payandeh, "Application of Visual Tracking for Robotic-Assisted Laparoscopic Surgery," Journal of Robotic Systems, vol. 19, No. 7, pp. 315-328, 2002.

Office Action mailed Sep. 3, 2014 for Japanese Application No. JP20120503535 filed Mar. 26, 2010.

Zhang, Lunwei et al., "FBG Sensor Devices for Spatial Shape Detection of Intelligent Colonoscope," IEEE International Conference on Robotics and Automation, Apr. 2004, New Orleans, Louisiana, pp. 835-840.

\* cited by examiner

CONTROLLER ASSISTED RECONFIGURATION OF AN ARTICULATED INSTRUMENT DURING MOVEMENT INTO AND OUT OF AN ENTRY GUIDE

CROSS REFERENCE TO RELATED APPLICATIONS

This application is a continuation-in-part to U.S. application Ser. No. 12/541,913 filed Aug. 15, 2009, which is incorporated herein by reference.

FIELD OF THE INVENTION

The present invention generally relates to controlling articulated instruments in medical robotic systems and in particular, to controller assisted reconfiguration of an articulated instrument during movement into and out of an entry guide for tool exchange and other purposes.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulated surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

A minimally invasive surgery may employ a number of different surgical instruments. When a different tool is desired during the surgical procedure, the surgical instrument may be withdrawn from the surgical site so that it can be removed from its associated arm and replaced with an instrument bearing the desired end effector. The desired surgical instrument is then inserted into the surgical site. A surgical instrument may also be withdrawn from a surgical site for reasons other than to replace the end effector. For example, the loading of a clip in a clip applier used in affixing tissue may occur outside the patient's body. In this case, each time a new clip is desired, the clip applier may be removed from the surgical site to load the clip and then reintroduced into the patient's body to apply the clip. As another example, removal of tissue or an object within a patient may involve grasping the tissue or object with an end effector while withdrawing the surgical instrument from the patient's body so that the tissue or object held by its end effector may be removed.

To perform a tool exchange for a medical robotic system, however, takes time. Moreover, it may be difficult to bring the new tool into the field of view manually after a tool exchange operation. It is also possible for the operator to misjudge the depth of insertion and place the tool too deep into the surgical site, which may cause unintended contact between the tool and the patient's anatomy. To avoid such contact, the operator is likely to move the new tool very slowly into the surgical site. These factors contribute to make a tool exchange operation a time-consuming process.

U.S. Pat. No. 6,645,196, which is incorporated herein by reference, describes a guided tool exchange procedure employable in a medical robotic system, such as the aforedescribed da Vinci® Surgical System, to guide a new tool quickly and precisely, after a tool exchange operation, into close proximity to the operating position of the original tool prior to its removal from a surgical site.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulated camera and a plurality of articulated surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

Due to the limited number of articulated instruments that may be disposed in the entry guide at one time, it may be necessary to exchange one articulated instrument in the entry guide for another instrument that performs a different function during the performance of a medical procedure. Alternatively, in lieu of exchanging the articulated instrument, only its end effector may be changed. As used herein, the phrase "tool exchange" is to be understood to cover both cases. To perform the tool exchange, the articulated instrument is retracted back into the entry guide and taken out through the entry guide's proximal end while other articulated instruments extending out of the distal end of the entry guide are either held in place or controlled by associated input devices. A new instrument (or old instrument with a new end effector) is then inserted into the entry guide and extended out of the entry guide's distal end. To retract the articulated instrument back into the entry guide, it may be necessary to first change the pose of the instrument (i.e., reconfigure its joints and links) so that it can be fully retracted into the entry guide. Since the instrument being retracted into the entry guide may be outside the field of view of an articulated camera instrument also extending out of and fixed in position relative to the distal end of the entry guide, possible collisions with other objects is a safety concern during blind retractions of an old tool into the entry guide from a surgical site and blind insertions of a new tool out of the entry guide towards the surgical site.

OBJECTS AND SUMMARY OF THE INVENTION

Accordingly, one object of one or more aspects of the present invention is a medical robotic system and method implemented therein which provides controller assisted reconfiguration of a pose of an articulated instrument during movement of the articulated instrument into and out of an entry guide for tool exchange and other purposes.

Another object of one or more aspects of the present invention is a medical robotic system and method implemented therein that places the articulated instrument into an entry pose so that the articulated instrument may be fully retracted into the entry guide in response to user initiated retraction of the articulated instrument towards and into the entry guide.

Another object of one or more aspects of the present invention is a medical robotic system and method implemented therein that places a new tool being extended out of an entry guide in the same pose that an old tool it has replaced was in prior to the tool exchange in response to user initiated insertion of the tool out of the entry guide.

Another object of one or more aspects of the present invention is a medical robotic system and method implemented therein that facilitates selective retraction/insertion of one or more articulated instruments into/out of an entry guide under user control while other articulated instruments extending out of the entry guide are either fixed in position or responsive to manipulation of associated input devices.

Still another object of one or more aspects of the present invention is a medical robotic system and method implemented therein that assists a user to perform a tool exchange without harming a patient or damaging any devices of the medical robotic system.

Yet another object of one or more aspects of the present invention is a medical robotic system and method implemented therein that provides sensory information to a user of the medical robotic system to aid the user in safely performing a tool exchange.

These and additional objects are accomplished by the various aspects of the present invention, wherein briefly stated, one aspect is a medical robotic system comprising: an entry guide; an articulated instrument disposed within the entry guide; means for allowing a user to command the articulated instrument to be retracted into the entry guide; and a controller configured to cause the articulated instrument to be reconfigured from a deployed pose in which the articulated instrument is incapable of being retracted into the entry guide to an entry pose in which the articulated instrument is capable of being retracted into the entry guide in response to the user commanding the articulated instrument to be retracted into the entry guide.

Another aspect is a method for moving an articulated instrument into and out of an entry guide, the method comprising: receiving a retraction command; determining whether a current configuration of the articulated instrument is in an entry pose in which the articulated instrument is capable of being retracted into the entry guide; causing the articulated instrument to be configured into the entry pose in response to the retraction command if the current configuration is determined not to be in the entry pose; and causing the articulated instrument to be retracted into the entry guide in response to the retraction command after the current pose is determined to be in the entry pose.

Additional objects, features and advantages of the various aspects of the present invention will become apparent from the following description of its preferred embodiment, which description should be taken in conjunction with the accompanying drawings.

DETAILED DESCRIPTION OF THE PREFERRED EMBODIMENT

Figure 1:
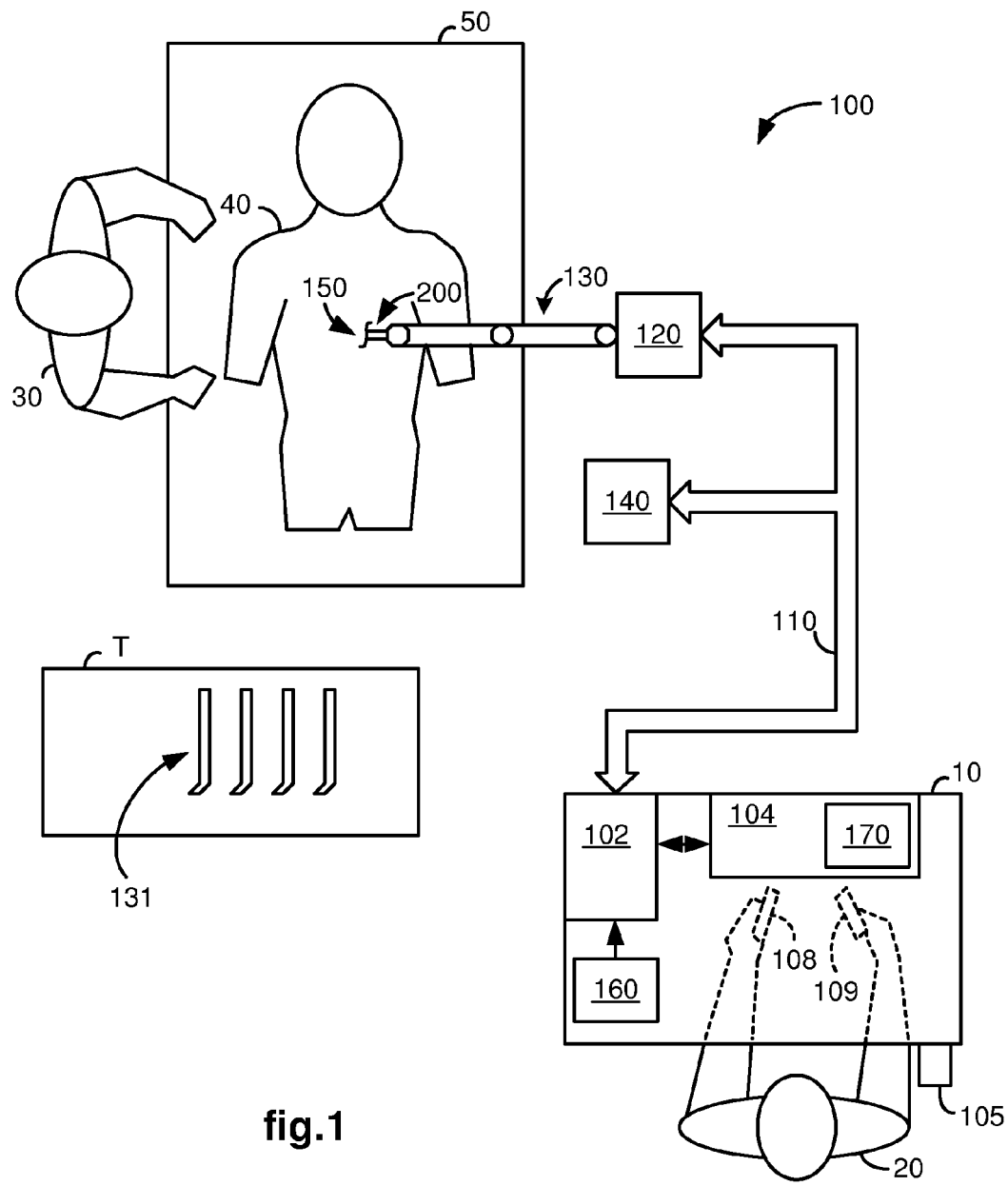
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150. The robotic arm assembly 130 is mounted on a stationary base 120. Also provided near the Patient is an auxiliary monitor 140 to be viewed by the assistant during the performance of a medical procedure on the Patient.

The console 10 includes a three-dimensional (3-D) monitor 104 for displaying a 3-D image of a surgical site to the Surgeon, left and right hand-manipulatable input devices 108, 109, and a processor 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
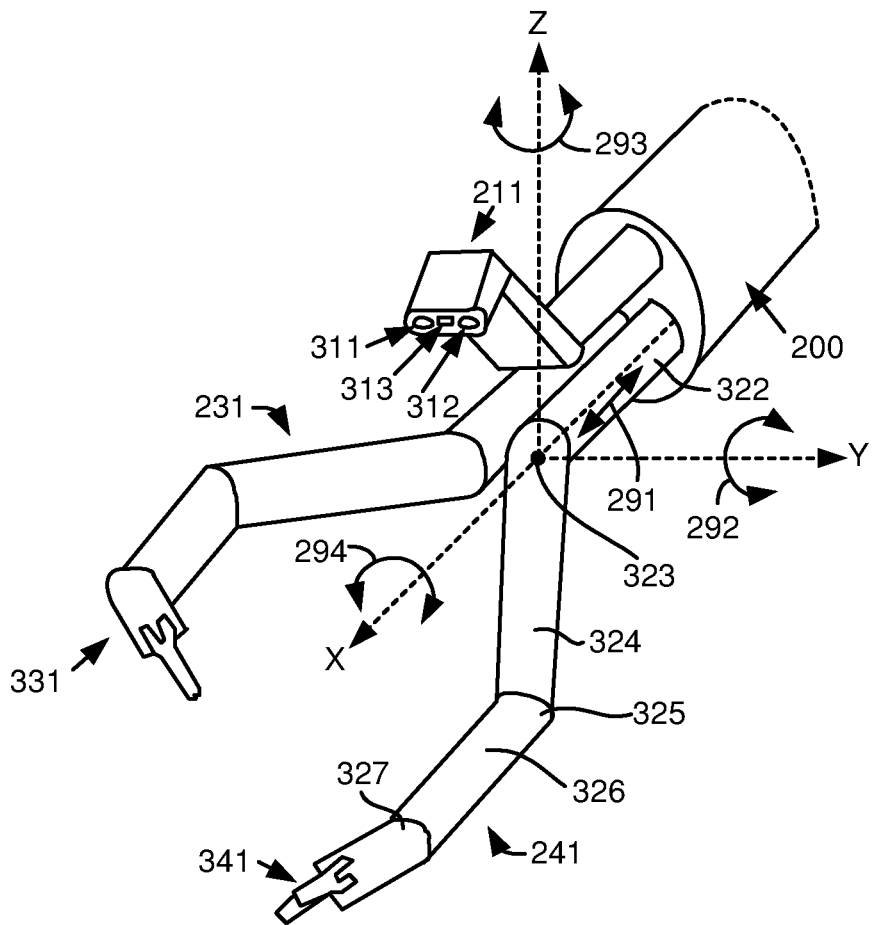
FIG. 3 illustrates a perspective view of a distal end of an entry guide with a plurality of articulated instruments extending out of it in a medical robotic system utilizing aspects of the present invention.
Figure 4:
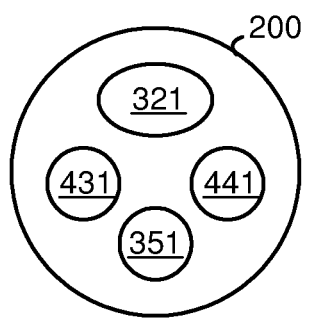
FIG. 4 illustrates a cross-sectional view of an entry guide as used in a medical robotic system utilizing aspects of the present invention.

As shown in FIG. 3, the entry guide 200 has articulated instruments such as articulated surgical tools 231, 241 and an articulated stereo camera 211 extending out of its distal end. The camera 211 has a stereo pair of image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in FIG. 4, passages 431, 441, 321 are available for extending the tools 231, 241 and camera 211 through the entry guide 200 and out of its distal end. Also, a passage 351 is available for extending another articulated surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the processor 102 causes corresponding movement of their respectively associated surgical tools 231, 241 while the Surgeon views the work site in 3-D on the console monitor 104 from real-time images of the work site captured by the articulated stereo camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence. By true presence, it is meant that the presentation of an image is a true perspective image simulating the viewpoint of an operator that is physically manipulating the end effectors 331, 341. Thus, the processor 102 transforms the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and implement various controllers described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

If it is necessary to change a tool being used during a procedure, the Assistant may remove the tool from the entry guide 200 and perform a tool exchange by replacing either the entire articulated instrument with another instrument or just its end effector with another end effector, such as the tool 131 from a Tray ("T") in the operating room wherein both the instrument and its end effector is referred to herein as a "tool". Either the Assistant or the Surgeon may control the retraction of the old tool back into the entry guide 200 for replacement and control the insertion (also referred to herein as "extension") of the new tool out of the entry guide 200 back to the surgical site. If the Surgeon wants the Assistant to perform the retraction and insertion of the tool, the Surgeon may directly instruct the Assistant to do so if they are within hearing distance of each other or the Surgeon may speak into a microphone on the console 10 so that the Assistant can hear the Surgeon's instructions on a headset or speaker. The Surgeon may also indicate to the Assistant which tool is to be exchanged by causing a light emitting diode ("LED") on the tool's manipulator to blink on and off. If the Assistant is to perform the retraction and insertion of the tool, then the tool is preferably disassociated from the input devices 108, 109 during the tool exchange, so that the Surgeon may use the input devices 108, 109 to operate other instruments in the medical robotic system 100.

Figure 2:
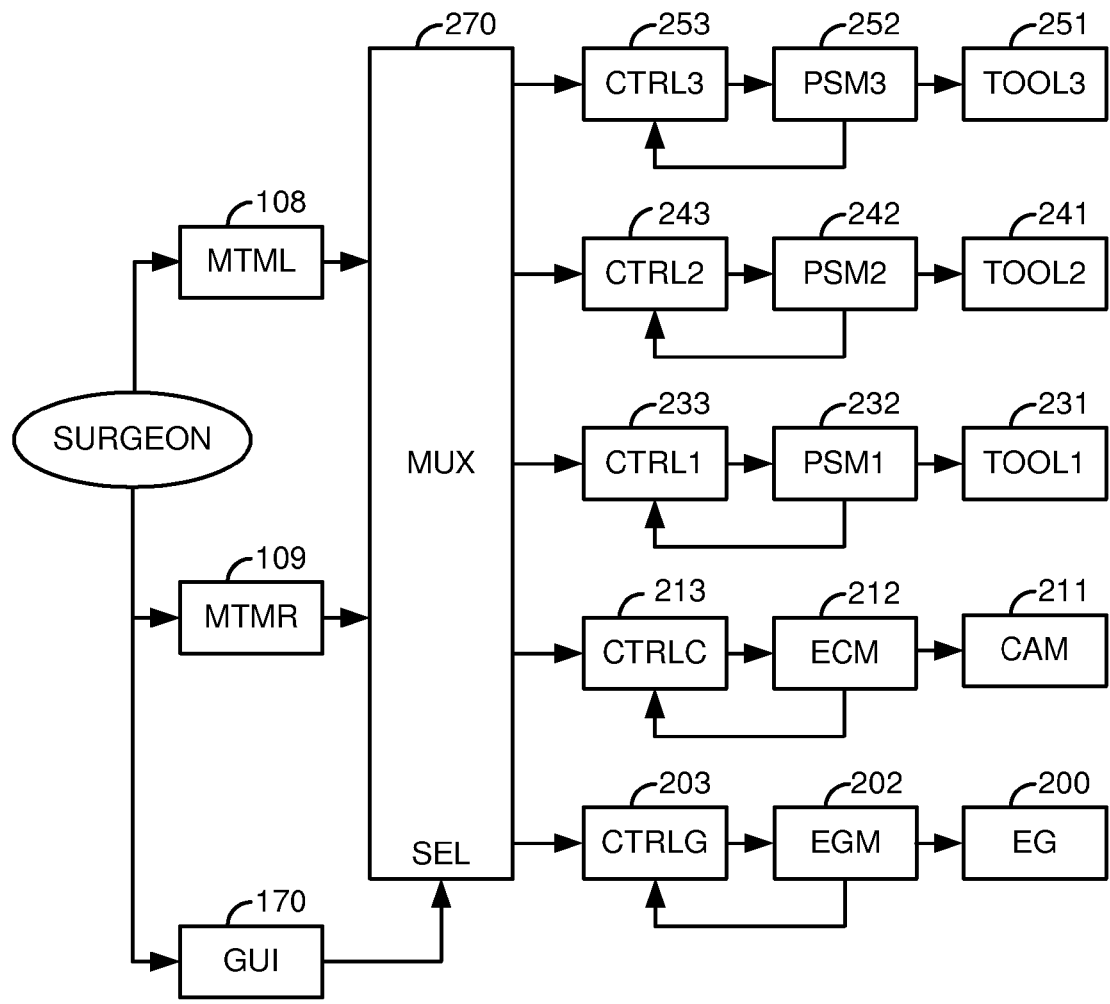
FIG. 2 illustrates a block diagram of components for controlling and selectively associating medical devices to left and right hand-manipulatable input devices in a medical robotic system utilizing aspects of the present invention.

FIG. 2 illustrates, as an example, a block diagram of components for controlling and selectively associating medical devices to the input devices 108, 109. Various surgical tools such as graspers, cutters, and needles may be used to perform a medical procedure at a work site within the Patient. In this example, three surgical tools (TOOL1, TOOL2, TOOL3) 231, 241, 251 are used to robotically perform the procedure and the camera (CAM) 211 is used to view the procedure. The tools 231, 241, 251 and camera 211 are inserted through passages 431, 441, 351, 321 in the entry guide 200. As described in reference to FIG. 1, the entry guide (EG) 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 251, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, the third surgical tool 251 is manipulated by a third tool manipulator (PSM3), and the entry guide 200 is manipulated by an entry guide manipulator (EGM) 202.

Each of the instrument manipulators 232, 242, 252, 212 is a mechanical assembly that carries actuators and provides a mechanical, sterile interface to transmit motion to its respective articulatable instrument. Each instrument 231, 241, 251, 211 is a mechanical assembly that receives the motion from its manipulator and, by means of a cable transmission, propagates the motion to its distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams, belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators.

As an example, as shown in FIG. 3, the second articulated instrument 241 comprises first, second, and third links 322, 324, 326, first and second joint assemblies (also referred to herein simply as "joints") 323, 325, and a wrist assembly 327. The first joint assembly 323 couples the first and second links 322, 324 and the second joint assembly 325 couples the second and third links 324, 326 so that the second link 324 may pivot about the first joint assembly 323 in pitch 292 and yaw 293 while the first and third links 322, 326 remain parallel to each other. The first, third, and camera articulated instruments, 231, 251, and 211, may be similarly constructed and operated.

The first and second joints 323, 325 are referred to as "joggle joints", because they cooperatively operate together so that as the second link 324 pivots about the first joint 323 in pitch and/or yaw, the third link 326 pivots about the second joint 325 in a complementary fashion so that the first and third links 322, 326 always remain parallel to each other. The first link 322 may also rotate around its longitudinal X-axis in roll 294 as well as move in and out in an insertion/retraction direction 291 (e.g., insertion towards the work site and retraction from the worksite) through the passage 441 of the entry guide 200. The wrist assembly 327 also has pitch and yaw angular movement capability so that the end effector 341 may be oriented up or down and to the right or left, and combinations thereof.

Thus, the manipulator 242 can manipulate the instrument 241 in four degrees of freedom movement. In particular, it has an insertion/retraction 291, roll 294 (about the longitudinal X-axis of the first link 281), pitch 292 (about a Y-axis which is orthogonal to the X-axis), and yaw 293 (about a Z-axis which is orthogonal to the X-axis and Y-axis) degrees of freedom movement. Manipulators 232, 252, 212 may also manipulate their respective instruments 231, 251, 211 in the same four degrees of freedom movement. Consequently, any of the instruments 231, 241, 251, 211 may be coupled to and manipulated by any of the manipulators 232, 242, 252, 212.

Each of the input devices 108, 109 may be selectively associated with one of the devices 211, 231, 241, 251, 200 through a multiplexer (MUX) 270 so that the associated device may be controlled by the input device through its controller and manipulator. For example, the Surgeon may specify the association through the GUI 170 for the left and right input devices 108, 109 to be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the surgical tool 251, camera 211 and entry guide 200 are each soft locked in place through their respective controllers 253, 213, and 203. If the Surgeon desires to control the surgical tool 251 using one of the input devices 108, 109, then the Surgeon may do so by simply disassociating the input device from its currently associated device and associating it instead to the tool 251. The Surgeon may then instruct the Assistant to perform a tool exchange for the disassociated tool.

As alternatives to the GUI 170 for providing selection input for the MUX 270, the selective association of the input devices 108, 109 to devices may be performed by the Surgeon using voice commands understood by the voice recognition system 160, and/or by the Surgeon depressing a button on one of the input devices 108, 109 or depressing the foot pedal 105, and/or using any other well known mode switching technique.

Figure 5:
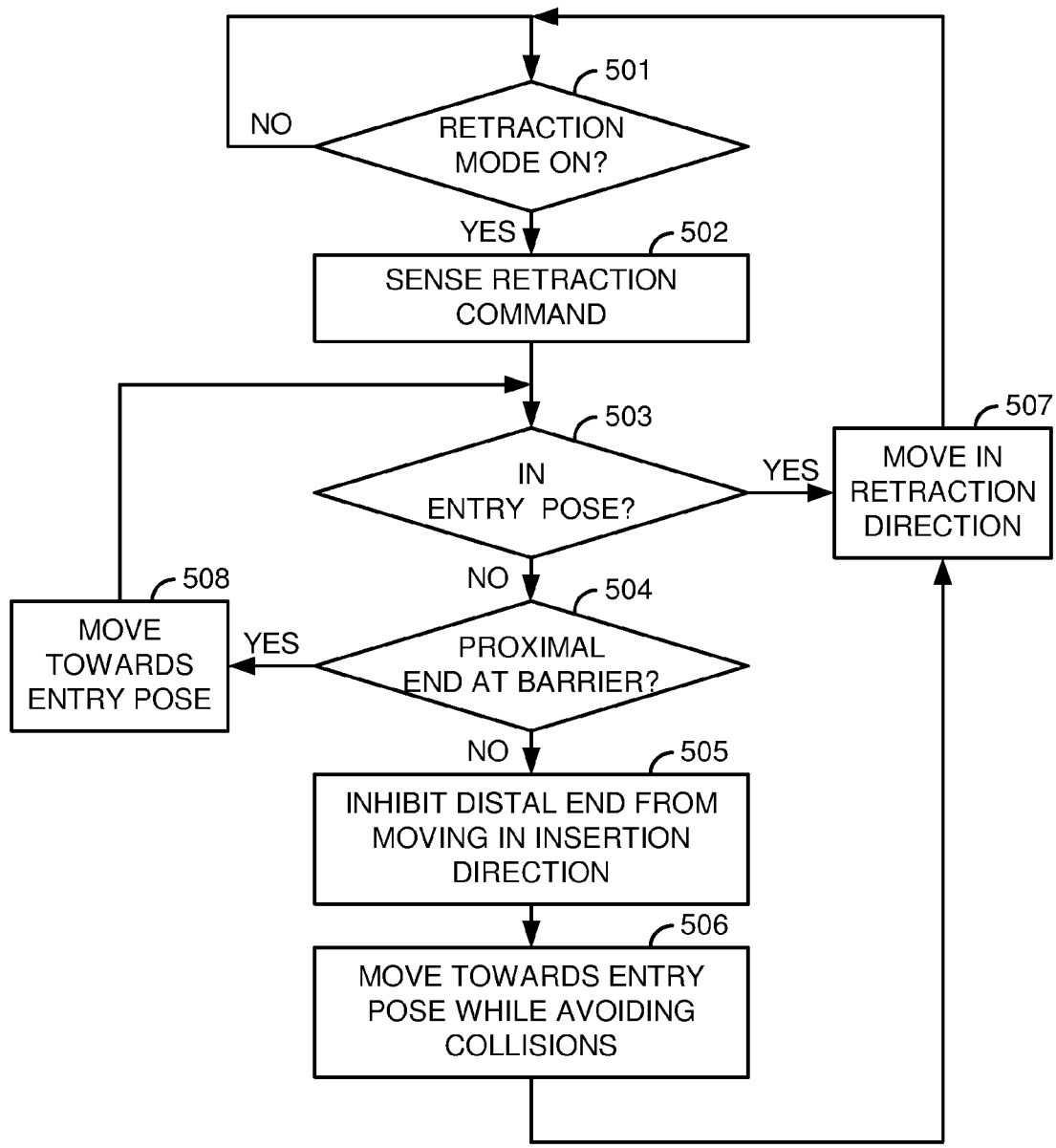
FIG. 5 illustrates a flow diagram of a method for controller assisted reconfiguration of an articulated instrument during user initiated movement of the articulated instrument into an entry guide, utilizing aspects of the present invention.
Figure 6:
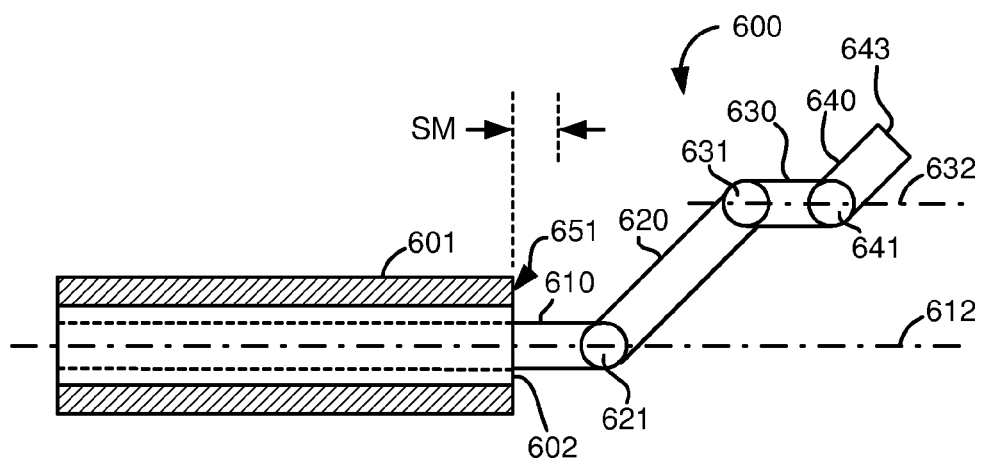
FIG. 6 illustrates a side view of an articulated instrument extending out of an entry guide in a deployed pose as used in a medical robotic system utilizing aspects of the present invention.

FIG. 5 illustrates, as an example, a flow diagram of a method preferably implemented in the processor 102 for controller assisted reconfiguration (i.e., changing the positions and/or orientations of joints and links) of an articulated instrument during user initiated and/or caused movement of the articulated instrument into an entry guide. A simplified example of such an articulated instrument is shown in FIG. 6, wherein an articulated instrument 600 extends out of a passage 602 of an entry guide 601. The articulated instrument 600 may be one of the instruments 211, 231, 241, in which case, the entry guide 601 may be the entry guide 200. Alternatively, the articulated instrument 600 may be a separate instrument extending through its own entry guide, in which case, the entry guide 601 may be a cannula. The entry guide 601 may be rigid, controllably flexible, or passively flexible.

Similar to the instrument 241, the articulated instrument 600 has an end effector 640, three joints 621, 631, 641, and three links 610, 620, 630 coupled to the joints as shown. Joints 621, 631 (referred to as "joggle joints") are constrained to move together in tandem so that the longitudinal axes 612, 632 respectively of links 610, 630 are always parallel to each other. In addition to being controllably rotated in pitch, the joint 621 may also be controllably rotated in a yaw about a yaw axis that is perpendicular to both the pitch axis and longitudinal axis 612. Although the joints 621, 631, 641 are shown as single joints, each of the joints 621, 631, 641 may comprise a plurality of joints, each of which in turn, provides a different degree-of-freedom movement. For example, the joint 621 may comprise both a pitch joint and a yaw joint that are slightly spaced apart from each other. In addition to joints 621, 631, 641, two additional joints are provided for manipulating the articulated instrument 600. A roll joint allows the link 610 and consequently, all the joints and links attached to it, to be controllably rotated in roll about the longitudinal axis 612 and a prismatic input/output (10) joint allows the link 610 and consequently, all the joints and links attached to it, to be controllably translated along the longitudinal axis 612. Since the roll and prismatic joints are dedicated to manipulating the link 610 of the articulated instrument 600, they are referred to herein as also being joints of the articulated instrument 600.

To initiate the method of FIG. 5, in 501, a determination is made whether the medical robotic system 100 is in a retraction mode. If the determination in 501 is NO, then the method continues to periodically perform 501 as indicated by the loop back arrow.

If the determination in 501 is YES, then in 502, the method monitors a user operated unit to sense a retraction command from the user. For example, the instrument manipulator (e.g., 232, 242) that manipulates the instrument 600 may be used for such a user operated unit, in which case, a button (or other type of switch) may be provided on or near the manipulator which when depressed by the Assistant 30, indicates that retraction mode has been entered so that the manipulator's controller (e.g., 233, 243) allows the Assistant 30 to manually move a part of the manipulator that causes the instrument 600 to move in and out of the entry guide 601 along the longitudinal axis 612. As another example, the input device (e.g., 108, 109) associated with the instrument 600 may be used for such a user operated unit, in which case, a button (or other type of switch) may be provided on or near the input device which when depressed by the Surgeon 20, indicates that retraction mode has been entered so that the controller associated with the input device allows the Surgeon 20 to teleoperatively cause the associated instrument 600 to move in and out of the entry guide 601. Other examples of a user operated unit that may be used by a user to enter retraction mode and issue retraction commands include the GUI 170, the voice recognition system 160 and the foot pedal 105.

Figure 7:
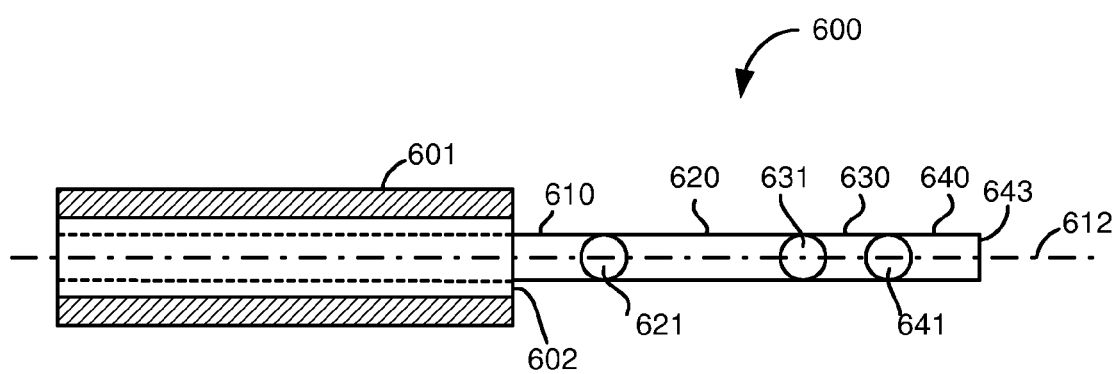
FIG. 7 illustrates a side view of an articulated instrument extending out of an entry guide in an entry pose as used in a medical robotic system utilizing aspects of the present invention.

After sensing a retraction command in 502, the method next determines in 503 whether the current configuration of the articulated instrument 600 is in an entry pose in which the instrument 600 can be fully retracted into the entry guide 601. An example of such an entry pose is shown in FIG. 7, wherein the configuration of the instrument 600 is such that the joints 621, 631, 641 are rotated so that the links 610, 620, 630 and the end effector 640 are all aligned so as to be retractable into the passage 602 of the entry guide 601. If the determination in 503 is YES (i.e., the articulated instrument 600 is in the entry pose), then in 507, the articulated instrument 600 is allowed to freely move in response to the retraction command and the method jumps back to 501 to process a next process cycle.

Figure 8:
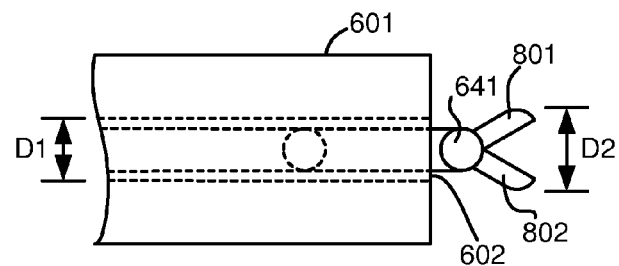
FIG. 8 illustrates a side view of an articulated instrument with open jaws extending out of an entry guide as used in a medical robotic system utilizing aspects of the present invention.

In addition to the end effector 640 preferably being lined up with the first link 610 in the entry pose as shown in FIG. 7, if the end effector 640 has open jaws 801, 802 such as shown in FIG. 8, then the jaws 801, 802 may be closed in coordination with the rest of the articulated instrument 600 so that the entry pose is understood to include the jaws 801, 802 being sufficiently closed so that their maximum displacement D2 is less than the diameter D1 of the passage 602 in the entry guide 601 in order to allow the instrument to be fully retracted into the entry guide 601. Alternatively, the jaws 801, 802 may be closed independently from the rest of the articulated instrument 600. For example, it may be desirable to wait until the jaws 801, 802 are near the distal end 651 of the entry guide 601 before closing them for safety reasons. In particular, since the jaws 801, 802 may be outside the field of view of the camera 211, blindly closing them may result in the jaws 801, 802 inadvertently harming tissue along the retraction path. One way to properly time the closing of the jaws 801, 802 is to only start closing them after an estimated position of the wrist joint 641 reaches a threshold distance (for a safety margin) from the distal end 651 of the entry guide 601. The position of the wrist joint 641 may be estimated in this case in a conventional manner along with the positions of all other joints and links of the articulated instrument 600 using sensed joint positions and inverse kinematics. Another way to properly time the closing of the jaws 801, 802 is by back driving a motor actuating (i.e., opening and closing) the jaws 801, 802 using force feedback to its controller as the jaws 801, 802 make physical contact with the distal end 651 of the entry guide 600. The force in this case may be sensed in any conventional manner such as by force sensors on the outer sides of the jaws 801, 802 or by a torque sensor for the motor actuating the jaws 801, 802.

If the determination in 503 is NO (i.e., the articulated instrument 600 is not in the entry pose), then the articulated instrument 600 is by default in a deployed pose in which the articulated instrument 600 is incapable of being fully retracted into the passage 602 of the entry guide 601, such as shown in the deployed pose of FIG. 6. In this case, before moving the articulated instrument 600 in the retraction direction, a determination is first made whether it is safe to do so in 504. In particular, a determination is made whether a proximal end (e.g., joint 621, which is the most proximal joint of the instrument outside of the entry guide) of the articulated instrument 600 is within a threshold distance or safety margin "SM" from the distal end 651 of the entry guide 601. The purpose of the safety margin is to prevent damage from occurring to either or both the entry guide 601 and the articulated instrument 600 when attempting to force the articulated instrument 600 through the passage 602 while it is in a configuration in which it physically will not fit at the time.

If the determination in 504 is NO (i.e., the safety margin has not been reached), then in 505-507, the method performs a number of tasks preferably concurrently through appropriate constraints placed in inverse kinematics equations used in the instrument's manipulator. In 505, the method inhibits a distal end 643 of the articulated instrument 600 from moving in an opposite direction from the retraction direction (i.e., in the insertion direction) beyond its initial position at the start of retraction while the method is changing the current configuration of the articulated instrument 600 towards the entry pose in 506 and moving the articulated instrument 600 in the retraction direction in response to the retraction command in 507. The rate that the method changes the configuration of the instrument to the entry pose is preferably related to the rate that the user is commanding the instrument to be retracted into the entry guide 601 and the initial distance of the proximal end of the articulated instrument 600 (i.e., its most proximal joint outside of the entry guide 601) from the distal end 651 of the entry guide 601. Thus, the faster the user commands the instrument 600 to be retracted, the faster the method changes its configuration to the entry pose; and the closer the proximal end of the instrument is to the distal end 651 of the entry guide 601, the faster the method changes the instrument's configuration to the entry pose.

Also, while performing 506, it is necessary for the method to avoid collisions with other instruments or harming the patient while moving the instrument 600 into its entry pose.

Figure 9:
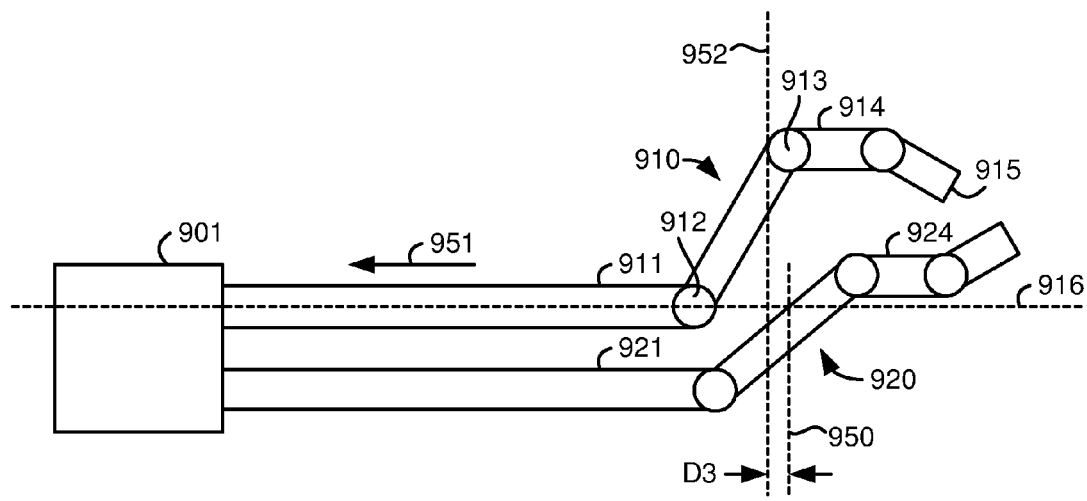
FIG. 9 illustrates a side view of two articulated instruments extending out of an entry guide as used in a medical robotic system utilizing aspects of the present invention.

For example, as shown in FIG. 9, two instruments 910, 920 extend out of an entry guide 901 in the same plane as their first links 911, 921. If the instrument 910 is immediately moved into its entry pose (by actuating joggle joints 912, 913), it may strike instrument 920 by either its link 914 or distal tip 915 striking link 924 of the instrument 920. To avoid collision, the instrument 910 may first be retracted in the direction 951 while holding its initial pose until its distal tip 915 passes a line 952, which is a distance D3 beyond a line 950 which is orthogonal to the longitudinal axis 916 of the first link 911 of the instrument 910 at the point where the instrument 920 intersects the longitudinal axis 916 of the instrument 910. The value of the distance D3 is chosen in this case to ensure that no part of the instrument 910 collides with any part of the instrument 920 during reconfiguration of the instrument 910 into its entry pose. Information of the joint and link positions of the instruments 910, 920 may be determined in a conventional manner using appropriately placed sensors.

Figure 10A:
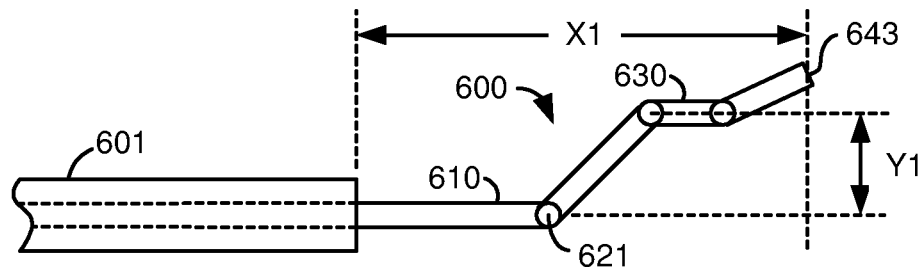
FIGS. 10a-10c illustrate side views of an articulated instrument for indicating how a distal tip of the articulated instrument is inhibited from moving in the insertion direction as the instrument is moved into an entry pose while being retracted into an entry guide in a medical robotic system utilizing aspects of the present invention.
Figure 10B:
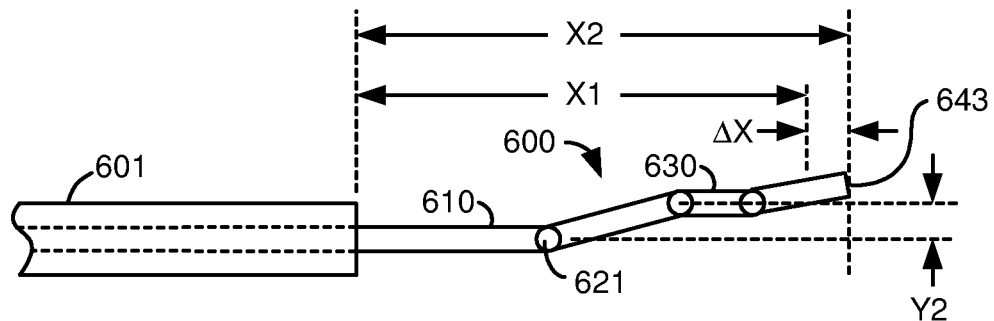
Figure 10C:
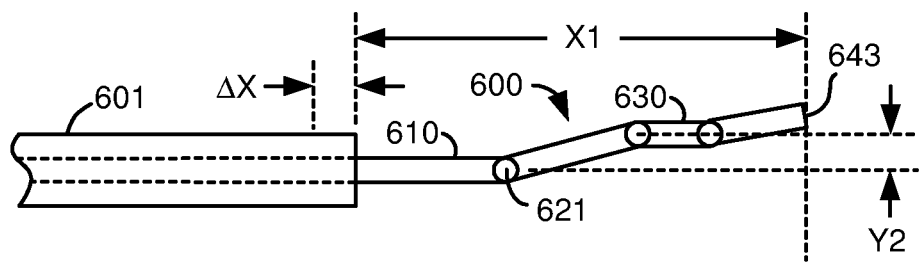

One technique that may be used for performing 505 is illustrated in FIGS. 10a-10c. In FIG. 10a, the articulated instrument 600 is shown in its initial deployed pose where the joggle joint angle is relatively large resulting in a distance Y1 between its parallel first and third links 610 and 630. Also, in this initial deployed pose, there is a distance X1 between its distal tip 643 and the distal end of the entry guide 601. In FIG. 10b, the articulated instrument 600 is shown with its current configuration moved towards the entry pose, but still in a deployed pose where the joggle joint angle has been reduced so as to result in a distance Y2, which is less than the initial distance Y1, between its parallel first and third links 610 and 630. It is important to note in this case that even though the proximal end of the articulated instrument 600 (e.g., proximal joint 621) has not moved, a distance X2 between its distal tip 643 and the distal end of the entry guide 601 results which is larger than the original distance X1, thus resulting in undesirable movement ΔX in the insertion direction. The movement is undesirable in this case because it may result in inadvertently striking an object such as an organ or other sensitive tissue in the patient and in so doing, result in damaging the object. Therefore, in FIG. 10c, the articulated instrument 600 is shown with its proximal end having been retracted by the amount ΔX. Thus, its distal tip 643 is held at the original distance X1 from the distal end of the entry guide 601. In 507, the distance ΔX is then added to the distance commanded by the retraction command and the articulated instrument 600 is moved accordingly. The method then jumps back to 501 to process sampled data for a next process cycle.

On the other hand, if the determination in 504 is YES (i.e., the distance between the proximal end of the articulated instrument 600 and distal end of the entry guide 601 is less than the safety margin), then the method inhibits the articulated instrument 600 from being retracted towards the entry guide 601, proceeds to 508 to move the current configuration of the articulated instrument 600 towards the entry pose, and then loops back to 503. Thus, once the safety margin distance is reached, no further retraction of the articulated instrument 600 is allowed until its configuration is in the entry pose. To provide an indication to the user that the retraction of the instrument 600 is being inhibited, haptic feedback in the form of a resistive force that is proportional to a difference between the current pose of the instrument 600 and the entry pose may be provided to the user operated unit so as to be felt by the user. As long as the user commands a retraction against the haptic force, the method continues to move the current configuration of the articulated instrument 600 towards the entry pose in 508. Conversely, if the user does not command a retraction against the haptic force, the current configuration remains in the same pose by causing its controller to soft lock in place. Once a determination is made in 503, however, that the instrument 600 is in the entry pose, the haptic force may be removed and the method jumps to 507 to allow the instrument 600 to be retracted into the entry guide 601 by looping through 501-503 and 507 until the retraction of the articulated instrument 600 is completed as indicated, for example, by the user turning the retraction mode off. After fully retracting the articulated instrument 600 out of the proximal end of the entry guide 601, it may then be removed so that either a new instrument 900 may be inserted in its place or a new end effector attached to it in place of the end effector 640.

After performing the tool exchange, it may be desirable to put the new articulated instrument into the configuration that the old articulated instrument was in before retraction so that the instrument appears in the same position in the field of view of an image capturing device and consequently, in an image that is captured by the image capturing device and displayed on a monitor to the surgeon. Placing the instrument in the same configuration (i.e., same positions for joints and links of the articulated instrument) may also have the advantage of eliminating or at least simplifying necessary re-alignment between the input device and the instrument's manipulator once complete operator control is re-established for the instrument through a control system used to teleoperate it.

Although the retraction of only a single articulated instrument 600 is described above, the method is also applicable and intended to cover the retraction of multiple articulated instruments at a time into the entry guide. For example, any two or more of the devices (e.g., tools 231, 241) may be retracted together into the entry guide 200 in response to user interaction with the user operated unit (e.g., one of the input devices 108, 109) while the other devices (e.g., camera 211, tool 251) are either held in place (e.g., camera 211) or manipulated (e.g., tool 251) by their associated manipulators (e.g., 252) in response to their associated input devices (e.g., one of the input devices 108, 109 which is not being used as the user operated unit for retraction purposes). In particular, two or more instruments extending out of the entry guide may be selected for retraction, for example, by the surgeon using the GUI 170 so that their respective controllers each implement the method described in reference to FIG. 5 in response to input received from a common user operating unit (while avoiding collisions with each other and other objects along their respective retraction paths).

Figure 11A:
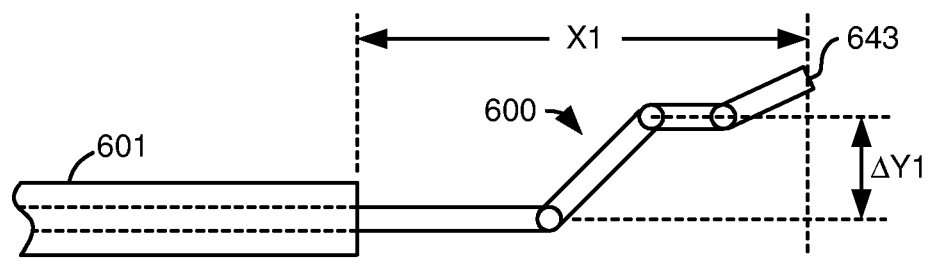
FIGS. 11a-11e illustrate a sequence of side views of articulated instruments during an instrument or tool exchange as performed in a medical robotic system utilizing aspects of the present invention.
Figure 11B:
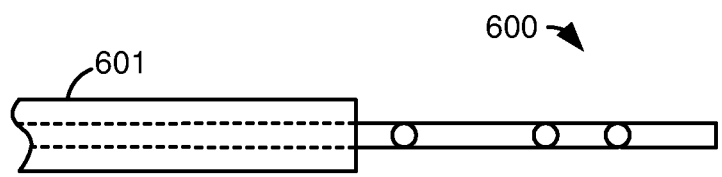
Figure 11C:
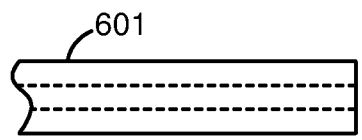
Figure 11D:
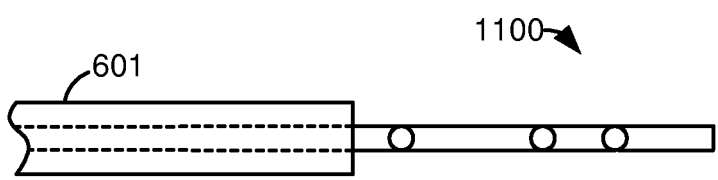
Figure 11E:
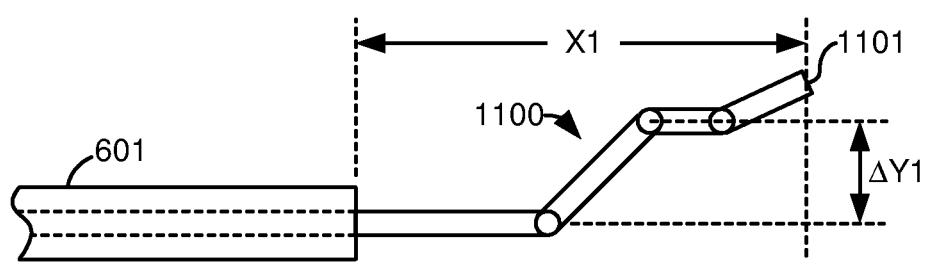

FIGS. 11a-11e illustrate, as an example, a sequence of side views of articulated instruments during an instrument or tool exchange as performed in the medical robotic system 100. In FIG. 11a, the instrument 600 is shown in its initial deployed pose in which its distal end 643 extends out a distance X1 from the distal end of the entry guide 601 (information of which is stored in a memory for later use) prior to retraction into the entry guide 601. In FIG. 11b, the instrument 600 is shown in an entry pose so that it may be retracted into the entry guide 601. In FIG. 11c, the instrument 600 has been fully retracted into the entry guide 601 and removed out of its proximal end. In FIG. 11d, a new instrument 1100 (or the old instrument with a new end effector) is being inserted towards the work site, initially coming out in the entry pose. Finally, in FIG. 11e, the new instrument 1100 is reconfigured to the initial deployed pose of the old instrument prior to initiation of its retraction into the entry guide 601 so that its distal end 1101 extends out the distance X1 from the distal end of the entry guide 601 (using the information previously stored in the memory) as the user commands the new instrument 1100 to be positioned back to the initial position of the old instrument 600 prior to its retraction (e.g., the deployed pose and position shown in FIG. 11a). A method similar to that described for retraction in FIG. 5 is preferably implemented in the new instrument's controller to assist the user in inserting the new instrument 1100 to the initial deployed pose of the old instrument 600 (e.g., assisting in reconfiguring the instrument from an initial entry pose to the deployed pose while avoiding collisions with other objects along the way and preventing the user from inserting the new instrument 1100 beyond the position of the old instrument 600 at the time retraction was initiated).

Figure 12:
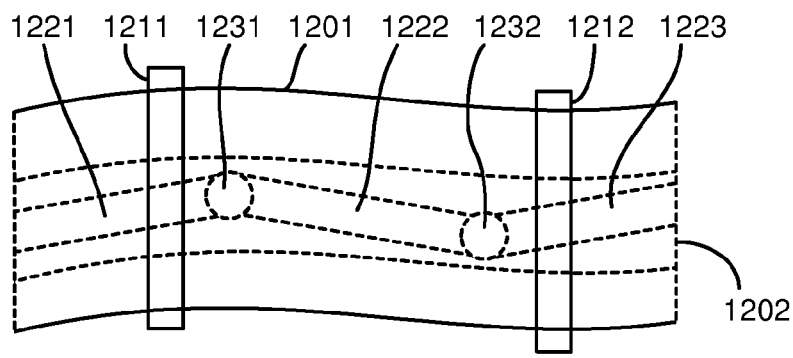
FIG. 12 illustrates a side view of a cut-out portion of a flexible entry guide with joints of an articulated instrument inside a passage of the entry guide as used in a medical robotic system utilizing aspects of the present invention.

Although a fixed configuration in which the longitudinal axes of the links 610, 620, 630 and end effector 640 all line up as shown in FIG. 7 is desired for their entry into the passage 602 of the entry guide 601, once one or more of the joints and links enter the passage 602, the configuration of the entered joints and links should change so as to conform to bending of the entry guide 601. As an example, FIG. 12 shows a cut-out portion of a flexible entry guide 1201 in which joints 1231, 1232 and links 1221, 1222, 1223 inside a passage 1202 of the entry guide 1201 have been reconfigured therein so that their configuration accommodates bending of the entry guide 1201 as determined from bend sensors appropriately spaced apart along the bendable length of the entry guide 1201, such as bend sensors 1211, 1212. Thus, as the entry guide 601 bends, the configuration of joints and links within the entry guide 601 are changed accordingly in 507 of FIG. 5 as the articulated instrument is retracted into the entry guide. Of course, if the entry guide 601 is rigid, then the joints and links of the instrument 600 preferably remain in the fixed configuration entry pose shown in FIG. 7.

Since the articulated instrument 600 may not be within the field of view of an image capturing device (such as the articulated stereo camera 211 extending out of the distal end of entry guide 200 as shown in FIG. 3) providing images to be viewed in a captured image area of the console monitor 104 as the instrument 600 is being retracted into the entry guide 601, it is desirable to assist the user controlling the retraction to receive some sensory cue of when the instrument 600 is nearing the distal end 651 of the entry guide 601 and its current pose. Although auditory signals may be used to indicate either the distance to the distal end 651 of the entry guide 601 or the closeness of the current pose of the instrument 600 to the entry pose, they cannot practically provide information on both at the same time. Accordingly, visual indications capable of providing such information are preferred means for providing such sensory cues.

Figure 13:
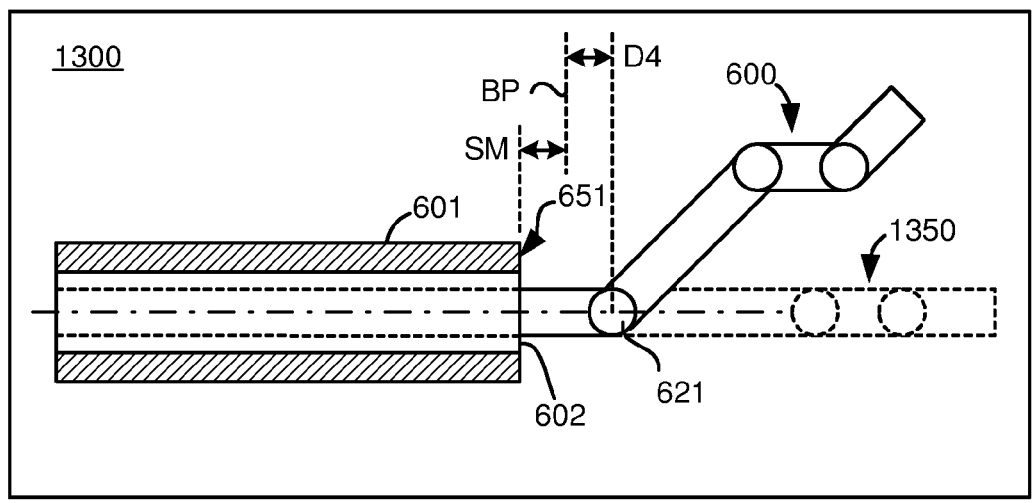
FIG. 13 illustrates computer generated auxiliary view of deployed and entry poses of an articulated instrument relative to an entry guide in a medical robotic system utilizing aspects of the present invention.
Figure 14:
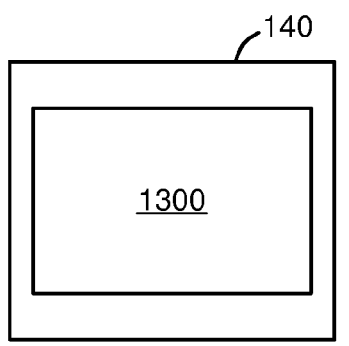
FIG. 14 illustrates computer generated auxiliary view being displayed on a patient-side monitor in a medical robotic system utilizing aspects of the present invention.
Figure 15:
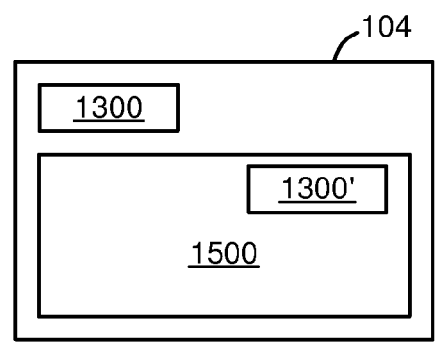
FIG. 15 illustrates computer generated auxiliary view being displayed on a surgeon console monitor in a medical robotic system utilizing aspects of the present invention.

FIG. 13 illustrates, as an example, a computer generated auxiliary view 1300 including graphical representations of currently deployed (indicated by solid line instrument 600) and target entry (indicated by dotted line instrument 1350) poses of the articulated instrument 600 relative to the distal end 651 of the entry guide 601 along with other information, such as a current distance D4 of a proximal joint 621 from a barrier point ("BP") providing the safety margin ("SM") as described in reference to FIG. 6 and used in 504 of FIG. 5, which assists a user in retracting the instrument 600 into the entry guide 601 in a medical robotic system. In addition to the instrument 600, the entry guide 601 and any other instruments extending out of the entry guide may also be shown so that if a collision between the instrument 600 and one of the other instruments is imminent, the auxiliary view 1300 would indicate it. A similar computer generated auxiliary view may be generated when the instrument 600 (or its replacement) is being inserted back out of the entry guide 601. The auxiliary view 1300 may then be viewed by the Assistant on the patient-side auxiliary monitor 140 as shown, for example, in FIG. 14 to assist the Assistant when the Assistant is controlling the retraction of the instrument 600 into the entry guide 601. Alternatively, the auxiliary view may be viewed by the Surgeon on the console monitor 104 as shown, for example, in FIG. 15 to assist the Surgeon when the Surgeon is controlling the retraction of the instrument 600 into the entry guide 601 using an associated one of the input devices 108, 109, or alternatively, a voice recognition system 160, a graphical user interface 170 or a foot pedal 105. As shown in FIG. 15, the auxiliary view 1300 may be displayed in an area (indicated by the reference number 1300) outside the captured image area 1500 or it may be displayed as an overlay (indicated by the reference number 1300') to the captured image area 1500. A similar computer generated auxiliary view may be generated and viewed when the instrument 600 (or its replacement) is being inserted back out of the entry guide 601.

The auxiliary view 1300 is useful information for the user because the user maintains primary control of the instrument while causing it to be retracted into or inserted out of the entry guide. In particular, although the instrument's controller reconfigures the instrument's pose during its movement into and out of the entry guide, such reconfiguration is in response to the user's action so that it may be stopped or reversed by the user stopping or reversing the direction of its movement. Thus, if the auxiliary view 1300 (or other sensory cue such as an audio cue, other visual cue, or haptic cue) indicates that the instrument is being placed in an unsafe position and/or configuration, the user may prevent it from doing so at any time. Further, if the user decides to abort the retraction of a tool into its entry guide for any reason, its controller using stored information of its initial deployed pose prior to retraction movement may assist the user in repositioning the tool to the initial deployed pose and position.

Although the various aspects of the present invention have been described with respect to a preferred embodiment, it will be understood that the invention is entitled to full protection within the full scope of the appended claims.

What is claimed is:

1. A medical robotic system comprising:
an entry guide;
an articulated instrument having a distal tip extending out of the entry guide; and
a processor;
the medical robotic system being programmed such that:
when the medical robotic system is operating in a retraction mode and in response to a user-commanded translational movement of the articulated instrument in a retraction direction into the entry guide, the processor automatically commands one or more rotational joints of the articulated instrument to be rotated from a deployed state, in which the articulated instrument is not fully retractable into the entry guide, to an entry state of the one or more rotational joints, in which the articulated instrument is fully retractable into the entry guide; and
when the medical robotic system is operating in a surgical mode and in response to a user-commanded input to surgically manipulate the articulated instrument, the processor commands one or more of the rotational joints of the articulated instrument to position the distal tip of the articulated instrument to perform a surgical operation.

2. The medical robotic system according to claim 1, wherein, when the medical robotic system is operating in the retraction mode and in response to the user-commanded translational movement of the articulated instrument in the retraction direction into the entry guide, the processor commands all movement of the articulated instrument to be inhibited except for the retraction of the articulated instrument into the entry guide and the rotation of the one or more rotational joints from the deployed state to the entry state.

3. The medical robotic system according to claim 1, wherein, when the medical robotic system is operating in the retraction mode and in response to the user-commanded translational movement of the articulated instrument in the retraction direction into the entry guide, the processor commands movement of the distal tip in an insertion direction to be inhibited while automatically commanding the one or more rotational joints to be rotated from the deployed state to the entry state.

4. The medical robotic system according to claim 1, wherein, when the medical robotic system is operating in the retraction mode and in response to the user-commanded translational movement of the articulated instrument in the retraction direction into the entry guide, the processor commands retraction of the articulated instrument into the entry guide to be inhibited when a most proximal joint of the one or more rotational joints of the articulated instrument is within a threshold distance to a distal end of the entry guide unless the one or more rotational joints of the articulated instrument are in the entry state.

5. The medical robotic system according to claim 1, further comprising:
an input device that is manipulatable by the user to teleoperate the articulated instrument,
wherein the processor commands haptic feedback to be provided to the input device wherein the haptic feedback indicates that retraction of the articulated instrument into the entry guide is being inhibited.

6. The medical robotic system according to claim 1, wherein the medical robotic system is programmed such that a collision between the articulated instrument and another object is avoided during rotation of the one or more rotational joints from the deployed state to the entry state.

7. The medical robotic system according to claim 1, wherein the entry guide is flexible and wherein the processor commands rotation of any of the one or more rotational joints of the articulated instrument that is inside the entry guide until a shape of the articulated instrument conforms to bending of the entry guide in response to the user-commanded translational movement of the articulated instrument in the retraction direction into the entry guide.

8. The medical robotic system according to claim 1, further comprising:
a switch; and
a manipulator for manipulating the articulated instrument, wherein the processor commands the manipulator to be manually movable by a user in response to activation of the switch, and wherein manual movement of the manipulator by the user generates the user-commanded translational movement of the articulated instrument in the retraction direction into the entry guide.

9. The medical robotic system according to claim 8, further comprising:
a button depressible by the user to indicate to the processor that the medical robotic system is operating in the retraction mode.

10. The medical robotic system according to claim 1, further comprising:
an input device manipulatable by the user to teleoperate the articulated instrument, wherein the user commands translational movement of the articulated instrument in the retraction direction into the entry guide by moving the input device in a corresponding manner, wherein the processor commands haptic feedback to be provided to the input device, and wherein the haptic feedback indicates a difference between a current state of the one or more rotational joints and the entry state of the one or more rotational joints.

11. The medical robotic system according to claim 1, wherein the articulated instrument has an end effector including a pair of jaws, and wherein the processor automatically commands movement of the pair of jaws into a closed position in coordination with commanding the rotation of the one or more rotational joints of the articulated instrument toward the entry state of the one or more rotational joints.

12. The medical robotic system according to claim 1, wherein the articulated instrument has an end effector including a pair of jaws, and wherein the processor commands movement of the pair of jaws into a closed position, independently of commanding the rotation of the one or more rotational joints to the entry state, by only starting to command closing the pair of jaws after the pair of jaws is retracted to a threshold distance from a distal end of the entry guide.

13. The medical robotic system according to claim 1, wherein, when the medical robotic system is operating in a surgical mode and in response to a user-commanded translational movement of the articulated instrument back to a position of the articulated instrument at which the medical robotic system entered the retraction mode, the processor automatically commands the one or more rotational joints of the articulated instrument to be rotated back to the deployed state of the one or more rotational joints.

14. The medical robotic system according to claim 1, wherein, after a tool exchange operation has been performed in which the articulated instrument has been retracted into the entry guide and replaced with a new articulated instrument and in response to a user-commanded translational movement of the new articulated instrument toward a position of the articulated instrument at which the medical robotic system entered the retraction mode, the processor automatically commands one or more rotational joints of the new articulated instrument to be rotated to a state corresponding to the deployed state of the one or more rotational joints of the articulated instrument.

15. The medical robotic system according to claim 1, wherein, when the medical robotic system is operating in a retraction mode, the processor commands a sensory indication to be provided to the user, wherein the sensory indication indicates at least one of: a distance of a most proximal of the one or more rotational joints from a distal end of the entry guide, and a difference between a current deployed state of the one or more rotational joints and the entry state of the one or more rotational joints.

16. The medical robotic system according to claim 15, wherein the sensory indication comprises a computer generated auxiliary view that is displayed on a monitor viewable by the user, and wherein the computer generated auxiliary view includes a graphic representation of the current deployed state of the one or more rotational joints.

17. The medical robotic system according to claim 16, wherein the computer generated auxiliary view includes a graphic representation of a barrier point located along a line of retraction of the articulated instrument and distal to the distal end of the entry guide, and wherein the computer generated auxiliary view includes an indication of a distance between the barrier point and a most proximal of the one or more rotational joints.

18. The medical robotic system according to claim 1, further comprising:
a second articulated instrument having a second distal tip extending out of the entry guide, wherein the medical robotic system is further programmed such that:
  when the medical robotic system is operating in the retraction mode and in response to a user-commanded translational movement of the second articulated instrument in a retraction direction into the entry guide, the processor automatically commands one or more rotational joints of the second articulated instrument to be rotated from a deployed state, in which the second articulated instrument is not fully retractable into the entry guide, to an entry state, in which the second articulated instrument is fully retractable into the entry guide; and
  when the medical robotic system is operating in the surgical mode and in response to user-commanded input to surgically manipulate the second articulated instrument, the processor commands one or more of the rotational joints of the second articulated instrument to position the second distal tip of the second articulated instrument to perform the surgical operation.

19. The medical robotic system according to claim 1, further comprising a second articulated instrument having a second distal tip extending out of the entry guide, wherein the medical robotic system is further programmed such that the second articulated instrument is placed in a locked operational state while the processor is automatically commanding the one or more rotational joints of the articulated instrument from the deployed state to the entry state.

20. The medical robotic system according to claim 1, further comprising a second articulated instrument having a second distal tip extending out of the entry guide, wherein the medical robotic system is further programmed such that the processor commands actuation of the second articulated instrument in response to user-commanded input to surgically manipulate the second articulated instrument while the processor is commanding rotation the one or more rotational joints of the articulated instrument from the deployed state to the entry state in response to the user-commanded translational movement of the articulated instrument in the retraction direction into the entry guide.

* * * * *